United States Patent
Yuan et al.

(10) Patent No.: US 12,078,637 B2
(45) Date of Patent: Sep. 3, 2024

(54) APPARATUS AND METHOD FOR ANALYZING PLATELET AGGREGATION

(71) Applicant: Medtronic Vascular, Inc., Santa Rosa, CA (US)

(72) Inventors: Charlene Yuan, Plymouth, MN (US); Trevor Huang, Maple Grove, MN (US); Tessy Kanayinkal, Maple Grove, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 443 days.

(21) Appl. No.: 17/203,030

(22) Filed: Mar. 16, 2021

(65) Prior Publication Data

US 2021/0318308 A1    Oct. 14, 2021

Related U.S. Application Data

(60) Provisional application No. 63/009,054, filed on Apr. 13, 2020.

(51) Int. Cl.
| | |
|---|---|
| *G01N 33/569* | (2006.01) |
| *B01L 3/00* | (2006.01) |
| *G01N 33/86* | (2006.01) |

(52) U.S. Cl.
CPC ........ *G01N 33/56966* (2013.01); *B01L 3/502* (2013.01); *G01N 33/86* (2013.01)

(58) Field of Classification Search
CPC ............. G01N 33/56966; G01N 33/86; G01N 2333/75; G01N 2333/755; G01N 2333/78; G01N 33/4905; B01L 3/502

USPC .......................................................... 422/407
See application file for complete search history.

(56) References Cited

U.S. PATENT DOCUMENTS

| | | | |
|---|---|---|---|
| 4,752,449 A | 6/1988 | Jackson et al. | |
| 5,174,961 A | 12/1992 | Smith | |
| 5,314,826 A | 5/1994 | Baugh | |
| 5,541,892 A | 7/1996 | Kobayashi et al. | |
| 5,626,209 A | 5/1997 | Viola | |
| 5,629,209 A * | 5/1997 | Braun, Sr. ............ | G01N 11/105 422/547 |
| 5,925,319 A | 7/1999 | Baugh et al. | |
| 5,951,951 A * | 9/1999 | Lane ...................... | G01N 33/86 422/561 |
| 6,010,911 A | 1/2000 | Baugh et al. | |
| 6,613,286 B2 | 9/2003 | Braun, Sr. et al. | |
| 8,921,115 B2 | 12/2014 | Yuan et al. | |
| 9,213,024 B2 * | 12/2015 | Sniadecki ............. | C12M 29/00 |
| 10,379,128 B2 | 8/2019 | Yuan et al. | |

(Continued)

FOREIGN PATENT DOCUMENTS

WO    WO-9506248 A1 *  3/1995  ............ C12M 35/06

*Primary Examiner* — Jill A Warden
*Assistant Examiner* — Jacqueline Brazin
(74) *Attorney, Agent, or Firm* — Mueting Raasch Group (57) ABSTRACT

A method carried out by a system configured to analyze platelet aggregation includes retaining a ferromagnetic object at an elevation of a chamber in which a sample of blood or plasma is disposed. The ferromagnetic object is retained at the elevation for a period of time. The ferromagnetic object is then released from the elevation. The ferromagnetic object minimal position is measured following the release of the ferromagnetic object. The object minimal position may be correlated with amount of platelet aggregation in the sample.

9 Claims, 5 Drawing Sheets

(56) References Cited

U.S. PATENT DOCUMENTS

2005/0233466 A1\* 10/2005 Wright ................. G01N 11/16
                                                    422/68.1
2014/0315228 A1   10/2014 Yuan et al.

\* cited by examiner

APPARATUS AND METHOD FOR ANALYZING PLATELET AGGREGATION

RELATED APPLICATION

The application claims the benefit of U.S. Provisional Patent Application No. 63/009,054, filed on Apr. 13, 2021.

FIELD

The present technology is generally related to apparatuses and methods for detecting changes in a property of a fluid, such as platelet aggregation in a sample comprising blood or plasma.

BACKGROUND

Platelets adhere to exposed sub-endothelium via collagen, plasma von Willebrand factor (VWF) and fibronectin. The adhesion activates platelets and causes platelet shape change and release of more chemicals to accelerate binding of platelets with fibrinogen, resulting in platelet aggregation. Platelet aggregation is important to the viability of platelets in terms of their normal function. There is a diagnostic need to assess patient's platelet function to maintain hemostasis management and reduce bleeding risk.

Platelet aggregation tests by impedance measurement or optical measurement are available commercially. Platelet aggregation tests based on impedance measurement may require large blood sample volume, such as 1 mL or more. Platelet aggregation test based on optical measurement may require removal of red blood cells. Such methods are generally not suitable for point-of-care platelet function monitoring.

SUMMARY

This disclosure generally relates to apparatuses, systems, and methods that provide for ready and informative analysis of platelet aggregation. Preferably, the apparatuses, system and methods are suitable for point-of-care platelet function analysis.

The apparatuses, systems, and methods are configured to detect platelet aggregation by correlating (a) movement of a ferromagnetic object in a chamber of a cartridge in which a sample of blood or plasma has been placed, with (b) platelet aggregation, where less movement is correlated with greater platelet aggregation.

In an aspect, the present disclosure provides a method carried out by a system configured to analyze platelet aggregation. The method includes retaining a ferromagnetic object, such as a ferromagnetic washer, at an elevation of a chamber in which a sample of blood or plasma is disposed. The ferromagnetic object is retained at the elevation for a period of time. For example, the ferromagnetic object may be retained at or near a top of the chamber. The ferromagnetic object may be retained by applying a magnetic force to retain the ferromagnetic object at the elevation. The ferromagnetic object may be retained for a time sufficient for platelet aggregation in the sample to occur. The ferromagnetic object is then released from the elevation. For example, the ferromagnetic object may be allowed to drop. The ferromagnetic object may be released by releasing a magnetic force that retains the object. The ferromagnetic object minimal position may be measured following the release of the ferromagnetic object. The object minimal position is the distance from a bottom of the chamber to the ferromagnetic object after the ferromagnetic object is released. The distance from the bottom of the chamber to the ferromagnetic object may be determined in any suitable manner. For example, the distance from the bottom of the chamber to the ferromagnetic object may be directly measured to determine the ferromagnetic object minimal position. As another example, the position of the ferromagnetic object in the chamber may be electromagnetically determined, and the distance of the ferromagnetic article from the bottom of the chamber may be determined based on the position.

The object minimal position may be correlated with platelet aggregation of the sample of blood or plasma. Greater object minimal positions may be correlated with greater platelet aggregation. Accumulation of aggregated platelets at the bottom of the chamber may raise the ferromagnetic object resting position, which increases the distance between the ferromagnetic object and the bottom of the chamber.

Depending on whether other components, such as antiplatelet agents and the like, are present in the chamber, platelet inhibition of activation may be determined. In some embodiments, the object minimal position is compared between different chambers having different components, where the different chambers are substantially identical other than the components contained therein.

In some embodiments, a platelet activator is present in the chamber. In some embodiments, a platelet activator is present in the chamber and no other exogenous clot enhancing agent is present in the chamber. In some embodiments, the platelet activator is adenosine diphosphate (ADP), collagen, or any other suitable natural or synthetic platelet activating agent.

In some embodiments, an anticoagulant is present in the chamber.

In some embodiments, at least a portion of an interior of the chamber is coated with a platelet binding molecule. In some embodiments, a bottom of the chamber is coated, a top of the chamber is coated, or the bottom and the top of the chamber is coated.

In some embodiments, the ferromagnetic object is a coated with a platelet binding molecule.

In some embodiments, a plurality of beads comprising a platelet binding molecule are present in the chamber. The beads may have a size in a range from about 2 micrometers to about 6 micrometers. The beads may comprise a plurality of beads coated with a platelet binding molecule. The beads may comprise polystyrene.

In some embodiments, the platelet binding molecule comprises fibrinogen, Type I collagen, or von Willebrand factor.

In an aspect, the present disclosure provides an article for use in a system configured to analyze platelet aggregation. The article comprises a ferromagnetic washer comprising a surface and a platelet binding molecule on the surface. The platelet binding molecule is on the surface prior to performing an assay to analyze platelet aggregation. For example, the platelet binding molecule may be coated on the surface of the ferromagnetic washer. Any suitable platelet binding molecule may be on the surface of the ferromagnetic washer. For example, the platelet binding molecule may comprise fibrinogen, Type I collagen, or von Willebrand factor.

The article may be disposed in a chamber of a cartridge for use in a system configured to analyze platelet aggregation. The chamber of the cartridge has an interior surface defining a top and a bottom.

A platelet binding molecule may be on at least a portion of the interior surface of the chamber. The platelet binding molecule is on the at least the portion of the interior surface of the chamber prior to performing an assay to analyze platelet aggregation. The platelet binding molecule may be coated on the at least the portion of the interior surface of the chamber. The at least the portion of the interior surface of the chamber may comprise the bottom, the top, or the top and the bottom.

In an aspect, the present disclosure provides a cartridge for use in a system configured to analyze platelet aggregation. The cartridge comprises a chamber having an interior surface defining a top and a bottom. A platelet binding molecule is on at least a portion of the interior surface of the chamber. The platelet binding molecule is on the at least the portion of the interior surface of the chamber prior to performing an assay to analyze platelet aggregation. The platelet binding molecule may be coated on the at least the portion of the interior surface of the chamber. The at least the portion of the interior surface of the chamber may comprise the bottom, the top, or the top and the bottom. The cartridge also comprises a ferromagnetic article disposed in the chamber.

The details of one or more aspects of the disclosure are set forth in the accompanying drawings and the description below. Other features, objects, and advantages of the techniques described in this disclosure will be apparent from the description and drawings, and from the claims.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising" and the like. As used herein, "consisting essentially of" as it relates to an composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein, a "washer" is a thin plate having a hole therethrough. The plate may be annular. The hole may be in the middle of the plate. The hole may be annular.

The present disclosure generally relates to apparatuses, systems, and methods for detecting platelet aggregation in a sample comprising blood or plasma. The apparatuses and methods are configured to detect platelet aggregation in a system by correlating movement of a ferromagnetic object in a chamber of a cartridge in which a sample of blood or plasma has been placed with platelet aggregation, where less movement is correlated with greater platelet aggregation.

Platelet aggregation may be measured in any suitable system, such as those described in U.S. Pat. Nos. 6,613,286 B2, 5,629,209, 8,921,115 B2, and 10,379,128 B2, each of which hereby incorporated herein by reference in its entirety to the extent that it does not conflict with the disclosure presented herein. In aspects, the description presented herein is tailored to systems and apparatuses that monitor or control movement of a ferromagnetic object through a sample. However, it should be understood that other suitable systems and apparatuses, in many cases, may be used to carry out the methods described herein.

Regardless of the type of system employed, a platelet aggregation analysis system includes a chamber into which a sample comprising blood or plasma may be introduced for analysis. The system is typically configured to mix the sample with one or more reagents that may affect platelet aggregation of the sample. For example, the system may employ sonic, ultrasonic or other waves, washers, plungers, rods, shaking, or the like to mix the sample and one or more reagents. In some examples, one or more reagents configured to prevent or inhibit clotting are in the chamber. In some examples, one or more reagents that enhance platelet aggregation are in the chamber. In some examples, one or more reagents that prevent or inhibit clotting and one or more reagents that enhance platelet aggregation are in the chamber, which may permit evaluation of platelet aggregation, and thus platelet function, in the absence of clotting.

The system is configured to monitor movement of a ferromagnetic object in the chamber and correlate such movement with platelet aggregation.

For example, the system may include one or more detectors for monitoring position of an object, such as a washer, determine whether platelet aggregation has occurred in the sample in the chamber of the cartridge. The system may include more than one chamber configured to contain a sample and different reagents, different concentrations of reagents, or different reagents and different concentrations of the reagents that affect platelet aggregation so that comparisons of platelet aggregation in the various chambers can be used to derive information regarding the platelet aggregation process, which may be used to assess platelet function.

Figure 1:
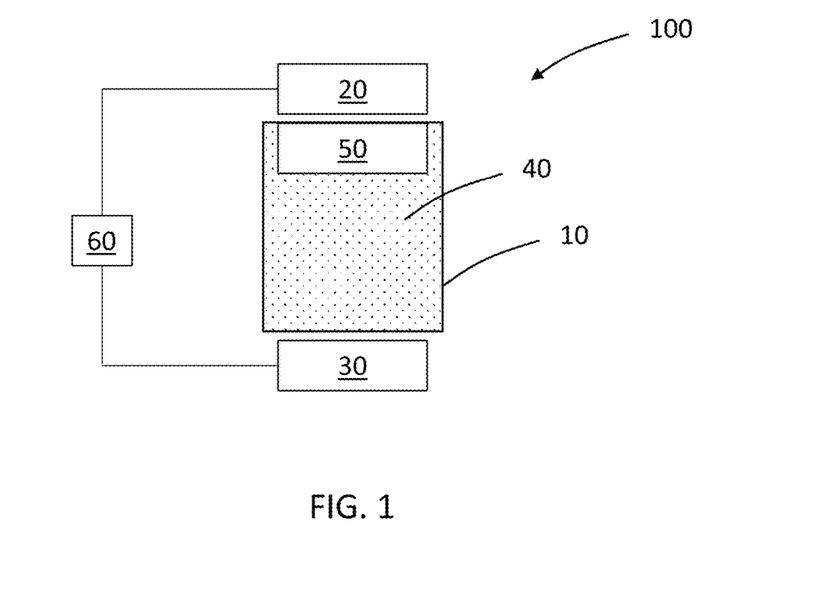
FIG. 1 is a schematic drawing of selected components of an embodiment of a platelet aggregation analysis system.

By way of example and with reference to FIG. 1, a schematic drawing of selected components of an example of a platelet aggregation analysis system 100 is shown. The depicted system 100 employs a ferromagnetic object 50 movable within a sample 40 contained in a chamber 10. In embodiments, the chamber 10 is configured to remain stationary during the testing process. The object 50 is moveable against gravity by electromagnet 20, which is operably coupled to electronics 60. For example, activation of the electromagnet 20 may cause the ferromagnetic object 50 to move to the top of the chamber 10 as shown in FIG. 1. The electronics 60 are configured to control activation of electromagnet 20. The position of the object 50 within the chamber 10 as object 50 falls through the sample 40 or rests after deactivation of the electromagnet 20 may be detected by sensor 30, which is also operably coupled to electronics 60. In embodiments where multiple chambers are employed, the electronics 60 are preferably configured to independently move a ferromagnetic object 50 in each chamber 10 without crosstalk. One or more detectors or sensors 30 may be employed to detect movement or monitor position of the objects 50 within individual chambers or among chambers.

Referring now to FIGS. 2-5, schematic diagrams illustrating features of various embodiments are shown. Only selected components of the systems 100 are shown in FIGS. 2-5.

Figure 2:
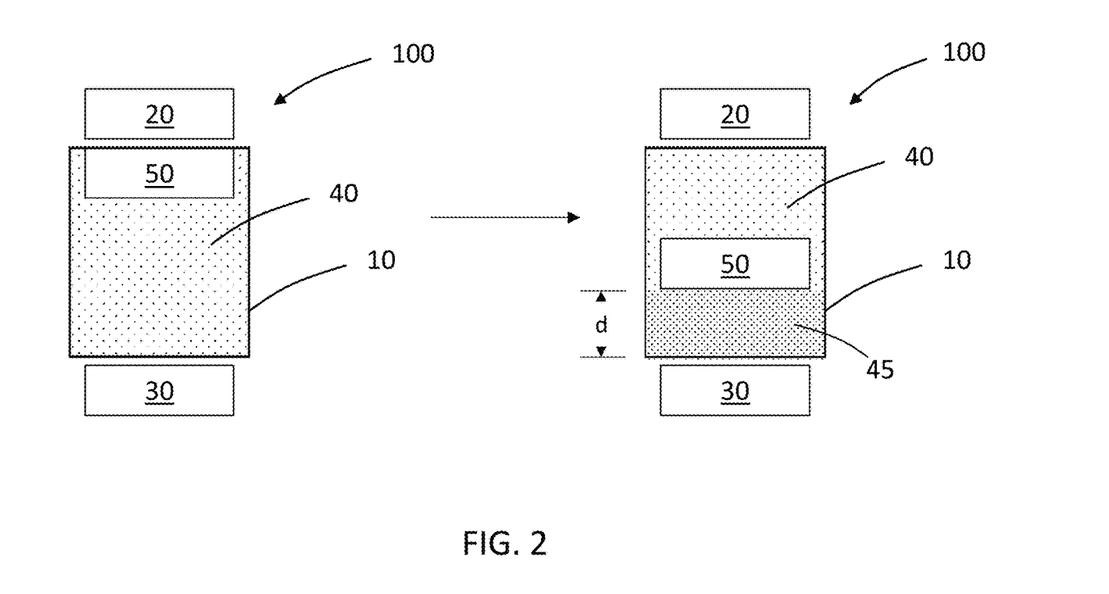
FIGS. 2-5 are schematic drawings of selected components of various embodiments of platelet aggregation analysis systems.

As shown in FIG. 2, the object 50 may be retained at the top of the chamber 10 by electromagnet 20 (see FIG. 2, left) for a period of time sufficient for platelet aggregation in the sample 40 to occur. After a sufficient period of time, the electromagnet 20 may be deactivated, allowing the object 50, such as a ferromagnetic washer, to drop through the sample. As shown in FIG. 2 (right), the object 50 rests on top of aggregated platelets 45 that have settled to the bottom of the chamber 10. The distance (d) from the object 50 to the bottom of the chamber 10 may be determined by sensor 30. Such a distance (d) is the object minimal position. The distance (d) is proportional to the amount of platelet aggregation that has occurred in the sample 40.

Figure 3:
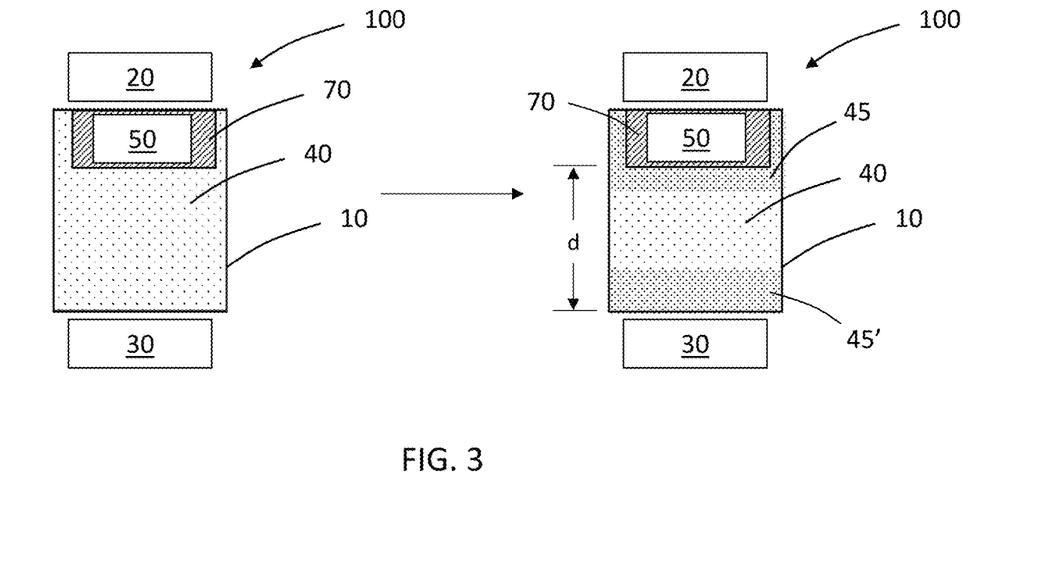

In the embodiment depicted in FIG. 3, the ferromagnetic object 50, such as a ferromagnetic washer, has a platelet binding molecule on its surface. In FIG. 3, a coating 70 comprising the platelet binding molecule is disposed on the object 50. The object 50 may be retained at the top of the chamber 10 by electromagnet 20 (see FIG. 3, left) for a period of time sufficient for platelet aggregation in the sample 40 to occur. After a sufficient period of time, the electromagnet 20 may be deactivated. If sufficient platelet aggregation has not yet occurred, the object 50 would drop through the sample 40. However, as shown in FIG. 3 (right), if a sufficient number of platelets 45 from the sample aggregate around and bind to the platelet binding molecule in the coating 70 disposed on the object 50, the platelet aggregation 45 may prevent to the object 50 from dropping through the sample 40. If the platelet aggregation 45 maintains the position of the object 50, the object minimal position (d) may be greater than if the object 50 had fallen through the sample 40 to rest on the aggregated platelets 45' that settled at the bottom of the chamber 10.

Figure 4:
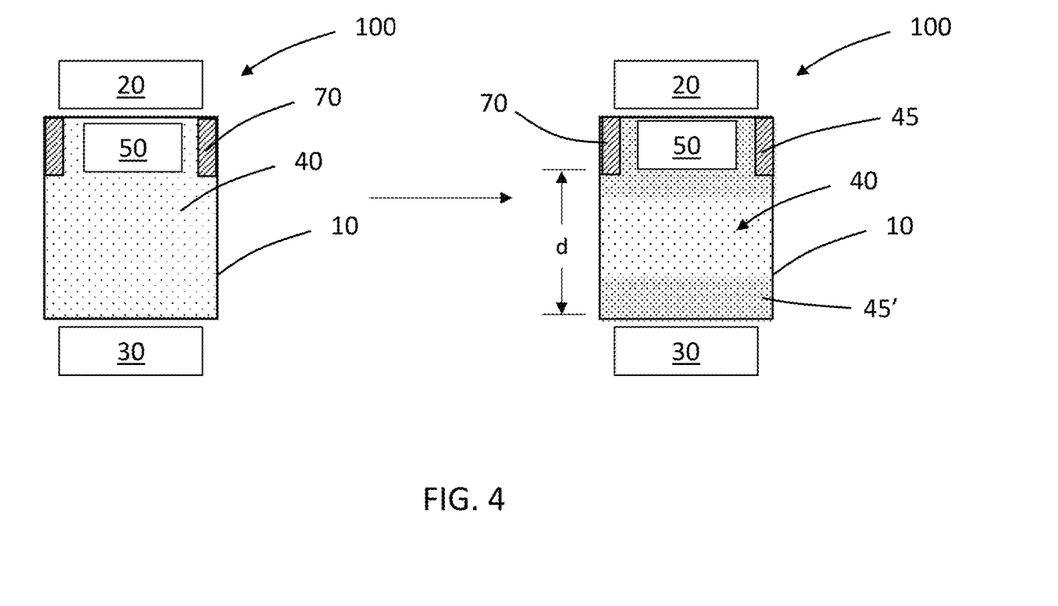

In the embodiment depicted in FIG. 4, a coating 70 comprising a platelet binding molecule is disposed on a portion of the interior surface of the chamber 10. The coating 70 is depicted as being coated near the top of the chamber 10 in FIG. 4 but may coat the entire inner surface or any suitable portion thereof. Regardless of where the coating is disposed, the presence of the platelet binding molecule may aid in platelet aggregation and increase the ultimate object minimal position. In FIG. 4, the object 50 is retained at the top of the chamber 10 by electromagnet 20 (see FIG. 4, left) for a period of time sufficient for platelet aggregation in the sample 40 to occur. After a sufficient period of time, the electromagnet 20 may be deactivated. If sufficient platelet aggregation has not yet occurred, the object 50 would drop through the sample 40. However, as shown in FIG. 4 (right), if a sufficient number of platelets 45 from the sample 40 aggregate around and bind to the platelet binding molecule in the coating 70 disposed on the inner surface of the chamber 10, the platelet aggregation 45 may prevent to the object 50 from dropping through the sample 40. If the platelet aggregation 45 maintains the position of the object 50, the object minimal position (d) may be greater than if the object 50 had fallen through the sample 40 to rest on the aggregated platelets 45' that settled at the bottom of the chamber 10.

Figure 5:
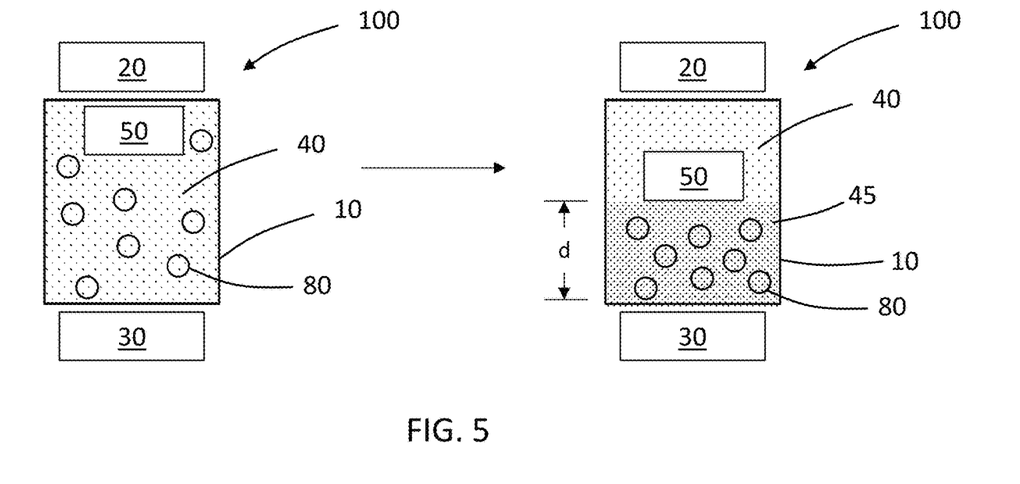

In the embodiment depicted in FIG. 5, a plurality of beads 80 are disposed in the chamber 10. The beads 80 may be mixed with the sample 40. The beads 80 comprise a platelet binding molecule. The beads 80 may be of any suitable size. Preferably, the beads 80 are sufficiently small to permit the object 50 to fall through the sample 40 in the chamber 10 if sufficient platelet aggregation fails to occur. As an example, the beads 80 may have a diameter from about 2 micrometers to about 6 micrometers. The beads 80 may be coated with platelet binding molecule. The beads 80 may be formed from any suitable material. For example, the beads 80 may be formed from or coated with any suitable polymer such as polystyrene or a hydrogel. Preferably, the beads 80 are of a density such that the beads 80 do not readily settle at the bottom of the chamber 10. For example, the beads 80 may be hydrogel beads.

Regardless of the beads 80 used, the beads 80 may increase the object minimal position (d) relative to systems that do not employ beads 80. As shown in FIG. 5, the object 50 is retained at the top of the chamber 10 by electromagnet 20 (see FIG. 5, left) for a period of time sufficient for platelet aggregation in the sample 40 to occur. The platelets 45 in the sample 40 bind to the beads 80 and settle to the bottom of the chamber 10 where they aggregate. After a sufficient period of time, the electromagnet 20 is deactivated, and the object 50 falls through the sample 40 to rest on aggregated platelets 45, which include beads 80. If the platelet aggregation 45 maintains the position of the object 50, the object minimal position (d) may be greater than if the object 50 had fallen through the sample 40 to rest on the aggregated platelets 45' that settled at the bottom of the chamber 10.

In the embodiments depicted in and discussed above regarding FIGS. 3-5, any suitable platelet binding molecule may be used. For example, the platelet binding molecule may include fibrinogen, Type I collagen, or von Willebrand factor, or platelet binding portions thereof.

Any of the embodiments depicted in FIGS. 2-5 may permit platelet aggregation detection in blood or plasma samples. The embodiments depicted in FIGS. 3-5 may be particularly beneficial in samples comprising blood because red blood cells may tend to settle to the bottom of the chamber, which because of the size of red blood cells may result in noise associated with measuring the object minimal distance. Because the embodiments depicted in FIGS. 3-5 are designed to increase the object minimal distance, signal-to-noise ratio may be enhanced. As such, the presence of red blood cells may not cause sufficient noise to overwhelm the signal caused by platelet aggregation in the sample.

Regardless of whether an exogenous platelet binding molecule is employed, platelet aggregation assays may be performed in multiple chambers, with object minimal position, and thus platelet aggregation, compared between chambers. For example, one chamber may include an exogenous platelet activator, another chamber may include an exogenous platelet inhibitor, and another cartridge may be free from exogenous platelet activators and inhibitors. Additional chambers may have different agents, different combinations of agents, different concentrations of agents, or combinations thereof. Platelet aggregation between chambers may be compared to gain insight into platelet aggregation within the sample.

Any suitable platelet activator, such as suitable natural or synthetic platelet activating agents, may be used. For example, collagen, adenosine diphosphate (ADP), epinephrine, arachidonic acid, platelet activating factor (acetyl-glyceryl-ether-phosphorylcholine) or combinations thereof may be used to activate platelets and enhance platelet aggregation.

Any suitable platelet inhibitor may be used. For example, a glycoprotein (GP)IIb/IIIa inhibitor, an ADP-induced platelet aggregation inhibitor, a cyclooxygenase (COX) activity inhibitor, a cyclic adenosine monophosphate (AMP) inhibitor, or combinations thereof may be used. Examples of glycoprotein (GP)IIb/IIIa inhibitors include Abciximab, Eptifibatide, Orbofiban, Roxifiban, Sibrafiban, and Tirofiban. Examples of ADP-induced platelet aggregation inhibitors include thienopyridines such as Clopidogrel, Prasugrel, and Ticlopidine; and nucleotide or nucleoside analogs such as Cangrelor, Elinogrel, and Ticagrelor. Examples of COX inhibitors include Acetylsalicylic acid, Aspirin, Aloxiprin, Carbasalate calcium, Indobufen, and Triflusal. Other platelet inhibitors include Dipyridamole, Picotamide, Terbogrel, Receptor antagonists Terbogrel, Terutroban, Cilostazol, Dipyridamole, Triflusal, Cloricromen, Ditazole, Vorapaxar and the like.

One or more of, such as all, the chambers may include an anticoagulant. Anticoagulants may inhibit clotting to allow monitoring of platelet aggregation (via object minimal position) in the absence of clotting. Any suitable anticoagulant may be used. Examples of suitable anticoagulants include coumarins, such as warfarin, heparin and heparin derivatives, such as low molecular weight heparin, inhibitors of factor Xa, such as fondaparinux, idraparinux, and idrabiotaparinux, thrombin inhibitors, and the like.

In some embodiments, the chambers do not include an exogenous clot enhancing agent, other than, perhaps, one or more platelet activating agent.

In some embodiments, the chambers are substantially identical other than the reagents contained within a chamber.

In some embodiments, a single cartridge that comprises a plurality of chambers may be used with a system to analyze platelet aggregation. The cartridge may be disposable. The chambers of the cartridge may comprise different agents, different combinations of agents, different concentrations of agents, or combinations thereof.

The chambers of the cartridge containing reagents may be platelet aggregation assay chambers or may be in communication with assay chambers of the cartridge where reagents from the reagent chamber are delivered to (e.g., drawn into or flow into) the clotting chamber for analysis.

Ferromagnetic objects, such as those depicted in and described regarding FIGS. 1-5, may be disposed in the assay chambers. The ferromagnetic object or the inner surface of the assay chamber may include a platelet binding molecule, such as depicted in and described regarding FIGS. 2-5.

Figure 6:
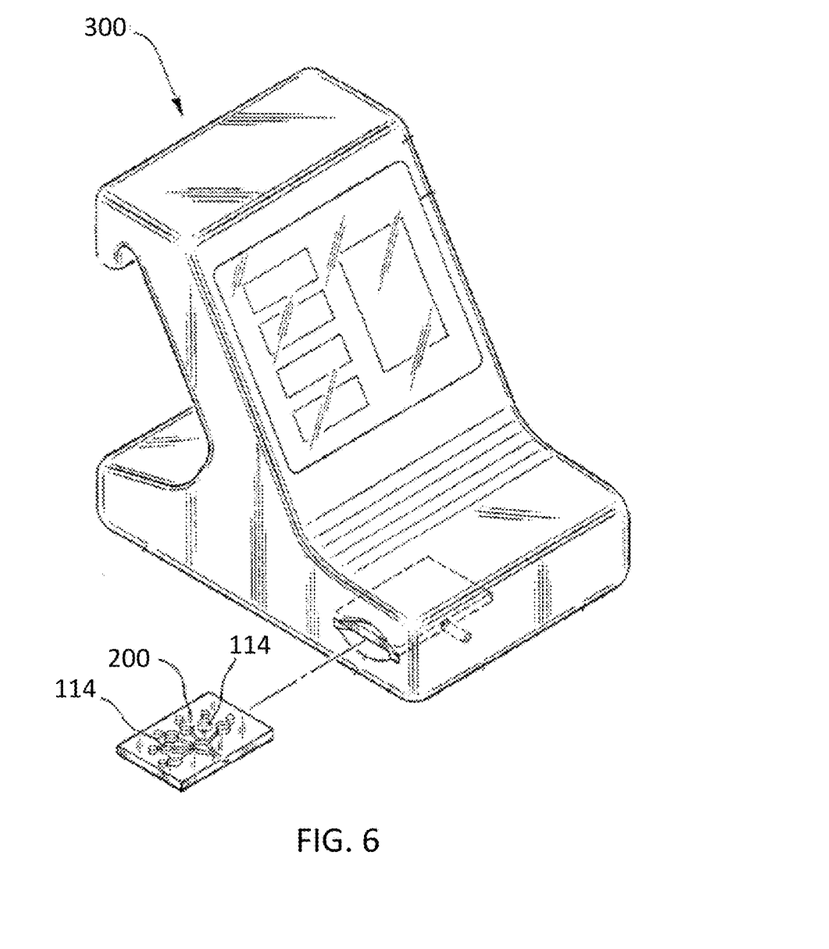
FIG. 6 is a schematic perspective view of an embodiment of a cartridge and a machine that may be used in accordance with the teachings presented herein.
Figure 7:
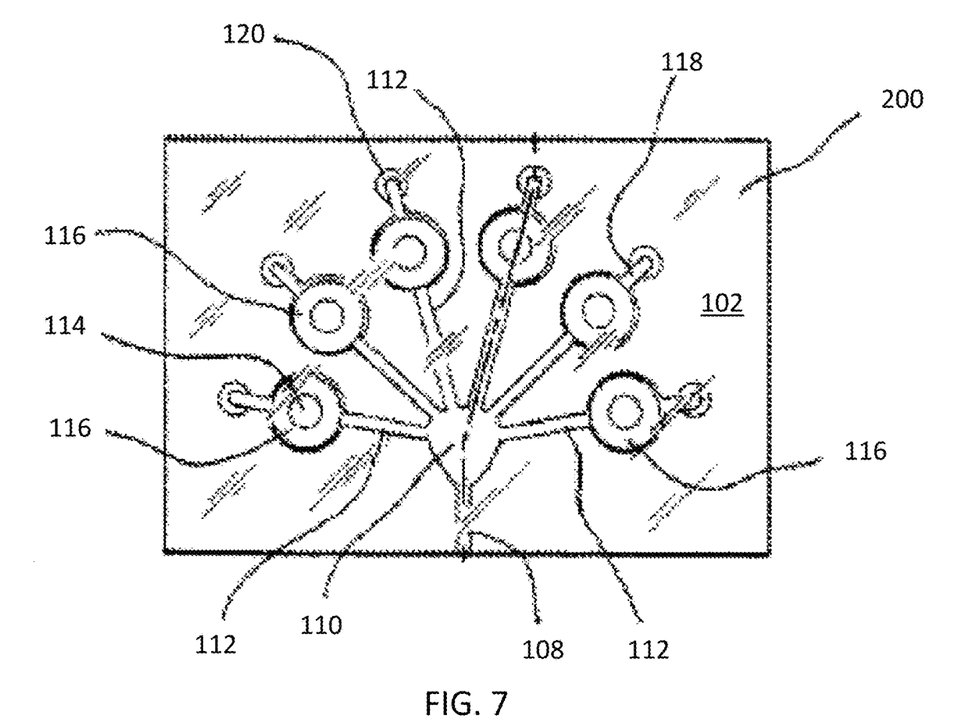
FIG. 7 is a schematic top plan view of an embodiment of a cartridge that may be used in accordance with the teachings presented herein.

Referring now to FIGS. 6-7 embodiments of a cartridge 200 and blood analyzer 300 are shown. Of course, cartridges and analyzers other than those depicted and described herein regarding FIGS. 6-7 may be used or modified to be used in accordance with the teachings presented herein. In some embodiments, cartridges and analyzers as described in U.S. Pat. Nos. 5,629,209 and 6,613,286 may be employed or modified to perform platelet aggregation assays as described herein.

FIG. 6 depicts an embodiment of a disposable cartridge 200 and associated platelet aggregation analysis device 300. The cartridge 200 and analyzer 300 comprise apparatus for detecting platelet aggregation, such as depicted in and discussed regarding FIGS. 2-5. In operation, the cartridge 200 may be inserted into the analyzer 300 before or after the cartridge is filled with the sample of blood or plasma to be tested. Preferably, the cartridge 200 is inserted into the analyzer 300 before the sample is introduced into the cartridge 200. Introducing the sample into the cartridge 200 after the cartridge 200 is inserted into the analyzer 300 provides a more consistent time for commencement of the platelet aggregation assay, provides for more consistent results associated with monitoring reaction time, if appropriate, and allows the assay to begin early in the platelet aggregation process.

The depicted cartridge 200 includes a plurality of fluid-receiving chambers 114. The analyzer device 300 then conducts an analytical test following a predetermined procedure in accordance with the type of analysis desired. By use of the cartridge 200, the analyzer 300 accurately, reliably, and quickly conducts tests to determine platelet aggregation. Some chambers of the cartridge 200 and the analyzer 300 with respect to those chambers may also conduct one or more tests, including, but not limited to, viscosity-related tests, for example, blood coagulation time tests, dose-response tests, and titration tests.

After a cartridge 200 containing a fluid sample is placed in the analyzer device 300, a ferromagnetic object such as the ferromagnetic washer 116 shown in FIG. 7 residing within an analysis chamber 114 is raised through the fluid sample, retained for a period of time sufficient to allow platelet aggregation, and allowed to drop. The analyzer device 300 then detects and measures the object minimal position of the washer 116 with a greater object minimal position correlating with increased platelet aggregation. The analyzer 300 may also detect other aspects of the washer 116 falling through the sample, such as the time required for the washer 116 to fall through the fluid sample.

A top view of an embodiment of a cartridge 200 is shown in greater detail in FIG. 7. The depicted cartridge 200 is substantially planar and formed of a rigid substantially integral material, for example, a plastic such as PETG (polyethylene terephthalate), that is, most preferably, inert with respect to the fluid sample being tested. The rigid material from which the cartridge 200 is formed may be partially or wholly transparent. The cartridge 200 may be manufactured as a unitary or monolithic piece (for example, by injection molding techniques), or the cartridge 200 may be assembled from various separate parts. In embodiments, a separate and distinct top (not shown) is attached to the cartridge 200 after a reagent is placed in the cartridge 200. In embodiments, the top is a heat sealable polyester film material such as Melinex®.

In the depicted embodiment, an injection port 108 is provided in a nominal front portion of the cartridge 200 for admission of the fluid sample into the cartridge 200. The injection port 108 directs the fluid sample into a fluid receiving/dispensing reservoir 110. From the fluid receiving/dispensing reservoir 110 the fluid proceeds through one or more conduits 112 to each conduit's respective analysis chamber 114. The motive force for this movement of the fluid through the cartridge 200 is provided by a fluid injection or pumping mechanism, for example, a manually activated syringe, or by other methods, such as by suction, for example, a vacuum system. Most preferably, each analysis chamber 114 is equidistant from the fluid receiving/dispensing reservoir 110, so that the fluid moves from the fluid receiving/dispensing reservoir 110 simultaneously or nearly so into each analysis chamber 114. Each analysis chamber 114 preferably has a volume of about 100 microliters to about 250 microliters. Although six fluid-receiving chambers 114 are shown in FIG. 7, it should be understood that any desired number of analysis chambers 114 in any desired orientation can be formed in the cartridge 200. Cartridges with other orientations, configurations, numbers, and sizes of any such analysis chamber 114 are contemplated herein.

Preferably, the multiple analysis chambers 114 are filled nearly simultaneously to ensure accuracy of the analytical test results. Such simultaneous or near-simultaneous filling may be accomplished by providing the fluid receiving/dispensing reservoir 110 with a substantially triangular configuration so that it acts as a uniform manifold to deliver the fluid to the analysis chambers 114.

Air contained in the cartridge 200 may be vented from the cartridge 200 as the fluid sample enters. In the depicted embodiment, a second conduit 118 leads from the analysis chamber 114 to an air vent/fluid plug device (not shown). As the fluid sample enters the cartridge 200 and moves into any given analysis chamber 114, air contained in the fluid receiving/dispensing reservoir 110, first conduit 112, and analysis chamber 114 is vented through the second conduit 118 and out of the cartridge 200.

One or more reagents may be mixed with the fluid sample in, or prior to entry to, an analysis chamber 114. The reagents may be placed in appropriate reagent chambers of the cartridge prior to completing assembly of the cartridge (e.g., securing the top to the cartridge). The reagent chambers may be the analysis chambers 114 or may be a chamber (not shown) in the path of a conduit 112 between the fluid receiving/dispensing reservoir 110 and an analysis chamber 114. The reagents are preferably dried, lyophilized, or the like to extend the shelf life of the cartridges that contain the reagents.

It will be understood that platelet aggregation analysis as described herein may be performed with the use of more than one cartridge or separate cartridges for each container. However, the use of a single cartridge provides for an easy to use and convenient apparatus.

A number of embodiments of methods, apparatuses, and systems are described herein. A summary of selected aspects of methods, devices and systems described herein is provided below.

In a first aspect a method carried out by a system configured to analyze platelet aggregation includes (a) retaining a ferromagnetic object at an elevation of a chamber in which a sample of blood or plasma is disposed, wherein the ferromagnetic object is retained at the elevation for a period of time; (b) releasing the ferromagnetic object from the elevation (allow ferromagnetic object to drop); and (c) measuring the ferromagnetic object minimal position following the release of the ferromagnetic object.

A second aspect is a method the first aspect, further comprising correlating the object minimal position with platelet aggregation of the sample of blood or plasma.

A third aspect is a method of the first or second aspect, wherein retaining the ferromagnetic object at the elevation of the chamber comprises retaining the ferromagnetic object at a top of the chamber.

A fourth aspect is a method of any one of the first three aspects, wherein measuring the object minimal position comprises measuring the distance of the ferromagnetic object from the bottom of the chamber.

A fifth aspect is a method any one of the first four aspects, wherein the period of time that the ferromagnetic object is retained at the elevation is a period of time sufficient for platelet aggregation in the blood or plasma to occur.

A sixth aspect is a method of any one of the first five aspects, wherein retaining the ferromagnetic object at the elevation comprises applying a magnetic force to retain the ferromagnetic object at the elevation.

A seventh aspect is a method of the sixth aspect, wherein releasing the ferromagnetic object comprises releasing the magnetic force.

An eighth aspect is a method of any one of the first seven aspects, wherein a platelet activator is present in the chamber.

A ninth aspect is a method of the eighth aspect, wherein no other exogenous clot enhancing agent is present in the chamber.

A tenth aspect is a method of the eighth or ninth aspect, wherein the platelet activator is adenosine diphosphate, collagen, or any other suitable natural or synthetic platelet activating agent.

An eleventh aspect is a method of any one of the first ten aspects, wherein an anticoagulant is present in the chamber.

A twelfth aspect is a method of any one of the first eleven aspects, wherein at least a portion of an interior of the chamber is coated with a platelet binding molecule.

A thirteenth aspect is a method of the twelfth aspect, wherein the at least the portion of the interior of the chamber comprises a bottom of the chamber.

A fourteenth aspect is a method of the twelfth or thirteenth aspect, wherein the at least the portion of the interior of the chamber comprises a top of the chamber.

A fifteenth aspect is a method of any one of the first fourteen aspects, wherein the ferromagnetic object is coated with a platelet binding molecule.

A sixteenth aspect is a method of any one of the first fifteen aspects, wherein a plurality of beads comprising a platelet binding molecule are present in the chamber.

A seventeenth aspect is a method of the sixteenth aspect, wherein the beads have a size in a range from 2 micrometers to 6 micrometers.

An eighteenth aspect is a method of the sixteenth or seventeenth aspect, wherein the beads comprise a plurality of polymeric beads coated with the platelet binding molecule.

A nineteenth aspect is a method of any one the sixteenth through the eighteenth aspects, wherein the beads comprise a polymer.

A twentieth aspect is a method of any of the twelfth through the nineteenth aspects, wherein the platelet binding molecule comprises fibrinogen, Type I collagen, or von Willebrand factor.

A twenty-first aspect is a method of any of the twelfth through the nineteenth aspects, wherein the platelet binding molecule comprises fibrinogen.

A twenty-second aspect is a method of any one of the first twenty-one aspects, wherein the ferromagnetic object comprises a ferromagnetic washer.

In a twenty-third aspect, an article for use in a system configured to analyze platelet aggregation includes a ferromagnetic washer comprising a surface; and a platelet binding molecule on the surface. The platelet binding molecule may be present on the surface in the absence of plasma or blood.

A twenty-fourth aspect is an article of the twenty-third aspect, wherein the platelet binding molecule is coated on the surface of the ferromagnetic washer.

A twenty-fifth aspect is an article of the twenty-third or twenty-fourth aspect, wherein the platelet binding molecule comprises fibrinogen, Type I collagen, or von Willebrand factor.

A twenty-sixth aspect is an article of the twenty-third or twenty-fourth aspect, wherein the platelet binding molecule comprises fibrinogen.

In a twenty-seventh aspect a cartridge for use in a system configured to analyze platelet aggregation includes a chamber having an interior surface defining a top and a bottom; and an article according to any one of claims twenty-third to twenty-sixth aspects disposed in the chamber.

A twenty-eighth aspect is a cartridge of the twenty-seventh aspect, wherein a platelet binding molecule is on at least a portion of the interior surface of the chamber.

A twenty-ninth aspect is a cartridge of the twenty-eighth aspect, wherein the at least the portion of the interior surface of the chamber comprises the bottom.

A thirtieth aspect is a cartridge of the twenty-eighth or twenty-ninth aspect, wherein the at least the portion of the interior surface of the chamber comprises the top.

A thirty-first aspect is a cartridge of any one of the twenty-eighth to thirtieth aspects, wherein the platelet binding molecule is coated on the at least the portion of the interior surface of the chamber.

A thirty-second aspect is a cartridge of any one of the twenty-eighth to thirty-first aspects, wherein the platelet binding molecule comprises fibrinogen, Type I collagen, or von Willebrand factor.

A thirty-third aspect is a cartridge of any one of the twenty-eighth to thirty-first aspects, wherein the platelet binding molecule comprises fibrinogen.

A thirty-fourth aspect is a cartridge for use in a system configured to analyze platelet aggregation including a chamber having an interior surface defining a top and a bottom, wherein a platelet binding molecule is on at least a portion of the interior surface of the chamber; and a ferromagnetic article disposed in the chamber. The platelet binding molecule may be on the interior surface in the absence of a fluid sample comprising blood or plasma.

A thirty-fifth aspect is a cartridge of the thirty-fourth aspect, wherein the platelet binding molecule is coated on the at least the portion of the interior surface of the chamber.

A thirty-sixth aspect is a cartridge of the thirty-fourth or thirty-fifth aspect, wherein the at least the portion of the interior surface of the chamber comprises the bottom.

A thirty-seventh aspect is a cartridge of any one of the thirty-fourth to thirty-sixth aspects, wherein the at least the portion of the interior surface of the chamber comprises the top.

A thirty eighth aspect is a cartridge of any one of the thirty-fourth to thirty-seventh aspects, wherein the platelet binding molecule comprises fibrinogen, Type I collagen, or von Willebrand factor.

A thirty-ninth aspect is a cartridge of any one of the thirty-fourth to thirty-seventh aspects, wherein the platelet binding molecule comprises fibrinogen.

A fortieth is a system configured to analyze platelet aggregation including a cartridge according to any one of the twenty-seventh to thirtieth aspects.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

"Electronics" may include a processor, memory, user interface, timer or counter, powers source or the like. Electronics may include any suitable processor, such as one or more microprocessors, DSPs, ASICs, FPGAs, programmable logic circuitry, or the like, and the functions attributed to the processor herein may be embodied as hardware, firmware, software or any combination thereof. Memory may store instructions that cause processor to provide the functionality ascribed to a system or apparatus described herein and may store information used by processor to provide the functionality ascribed to a system or apparatus described herein. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A power source may deliver operating power to components of a system or apparatus described herein. Power source may be an AC or DC power source, such as a battery and a power generation circuit to produce the operating power.

EXAMPLES

In the following, non-limiting Examples are provided to illustrate proof of concept of various embodiments of the methods, apparatuses and systems described herein.
Platelet Rich Plasma Platelet rich plasma (PRP) containing 1.5 U/mL heparin was filled into a six-channel cartridge similar to cartridge 200 depicted in and described regarding FIG. 7 for use with an analyzer similar to analyzer 300 depicted in and described regarding FIG. 6. The analyzer and cartridge were similar to those described in U.S. Pat. Nos. 5,629,209 and 6,613,286.

One chamber of the cartridge contained ADP such that the concentration in the chamber was 20 micromolar after introduction of the sample. Another chamber included no ADP. No other clot enhancing agent was in the sample or chamber of the cartridge. The chambers included a ferromagnetic washer. The cartridge was inserted in the analyzer before PRP sample fill. Immediately after the sample introduction, the test began, and platelet aggregation was analyzed.

The analyzer was programmed to hold the washer (disk) at the top of the chamber for 90 to 95% of the test cycle (a test cycle is the time sum of lift time and drop time), which was about 4.5 seconds for a test cycle of 5 seconds, to ensure platelets in the test sample aggregated and accumulated at the bottom of the chamber. The washer was allowed to drop (electromagnet deactivated), and the washer minimum position was determined by the proximity sensor (e.g., sensor 30 depicted in and described regarding FIGS. 2-5) in the presence and absence of ADP.

Figure 8:
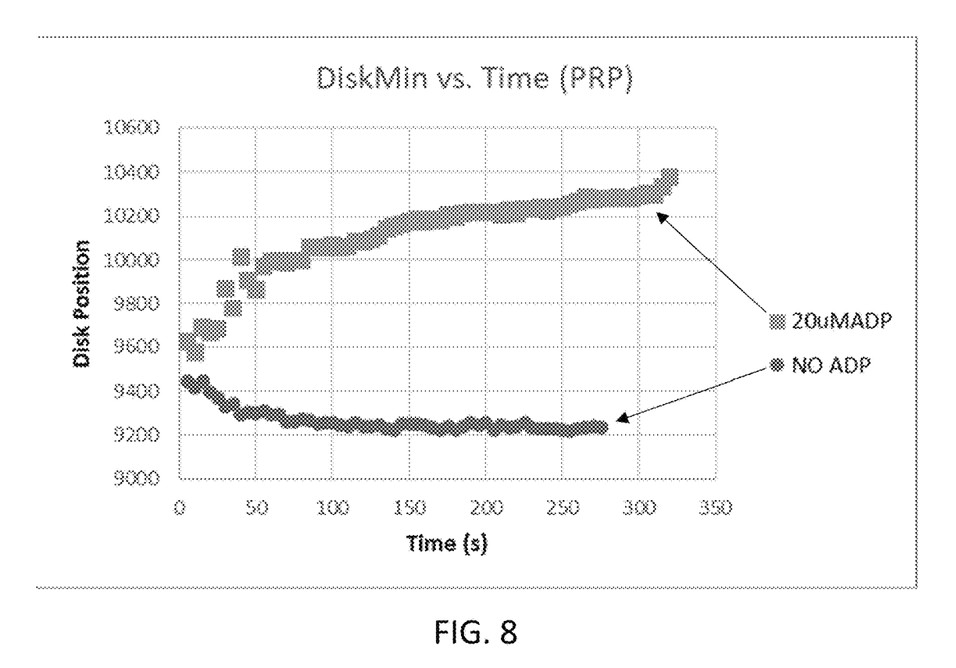
FIG. 8 is a graph of minimum position versus time for a washer in a platelet rich plasma sample in the presence and absence of adenosine diphosphate (ADP).

The results are shown in FIG. 8, which illustrates that the washer (disk) minimum position increased in the presence of ADP, a platelet activator, relative to in the absence of ADP. It is noted that heparin binds to human platelets and can cause activation and aggregation. Heparin is also an anticoagulant and it is used in this experiment to delay the clotting event and make sure the observed change in disk minimal position is due to platelet aggregation, not the viscosity changes of the sample due to clotting. The disk minimum position in ADP presence chamber increases as ADP induced platelet aggregation event took place, while the disk minimum position in the ADP absence chamber did not increase at the same test.
Platelet Poor Plasma Platelet poor plasma (PRP) containing 1.5 U/mL heparin was filled into a six-channel cartridge similar to cartridge 200 depicted in and described regarding FIG. 7 for use with a blood analyzer similar to analyzer 300 depicted and described regarding FIG. 6. The analyzer and cartridge were similar to those described in U.S. Pat. Nos. 5,629,209 and 6,613,286.

A chamber of the cartridge contained ADP such that the concentration in the chamber was 20 micromolar after introduction of the sample. No other clot enhancing agent was in the sample or chamber of the cartridge. The chambers included a ferromagnetic washer. Following introduction of the sample after the cartridge was inserted into the blood analyzer, the test was started, and platelet aggregation was analyzed.

The blood analyzer was programmed to hold the washer (disk) at the top of the chamber for 90 to 95% of the test cycle (a test cycle is the time sum of lift time and drop time), which was about 4.5 seconds for a test cycle of 5 seconds, to ensure platelets in the test sample aggregated and accumulated at the bottom of the chamber. The washer was allowed to drop (electromagnet deactivated), and the washer minimum position was determined.

Figure 9:
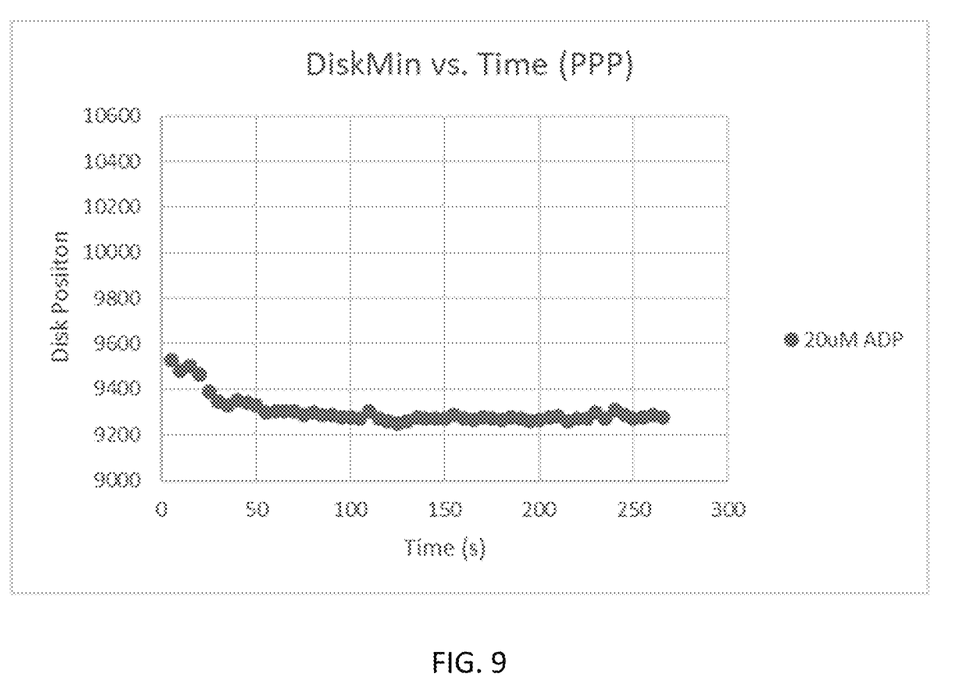
FIG. 9 is a graph of minimum position versus time for a washer in a platelet poor sample in the presence of ADP.

The results are presented in FIG. 9. With platelet poor plasma, the disk minimal position did not increase in the presence of ADP because platelet is not present in the sample.

CONCLUSION

The results presented in FIG. 8 and FIG. 9 illustrate that platelet aggregation event can be detected by the washer (disk) minimal position change in the apparatus similar to those described in U.S. Pat. Nos. 5,629,209 and 6,613,286.

Thus, embodiments of APPARATUS AND METHOD FOR ANALYZING PLATELET AGGREGATION are disclosed. One skilled in the art will appreciate that the apparatuses, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

What is claimed is:

1. A method carried out by a system configured to analyze platelet aggregation, the method comprising: retaining a ferromagnetic object at an elevation of a chamber in which a sample of blood or plasma is disposed, wherein the ferromagnetic object is retained at the elevation for a period of time, wherein the period of time that the ferromagnetic object is retained at the elevation is a period of time sufficient for platelet aggregation in the blood or plasma to occur; releasing the ferromagnetic object from the elevation to allow the ferromagnetic object to drop; measuring the ferromagnetic object minimal position following the release of the ferromagnetic object, wherein the object minimal position is the distance from a bottom of the chamber; and
further comprising correlating the object minimal position with platelet aggregation of the sample of blood or plasma.

2. The method of claim 1, wherein retaining the ferromagnetic object at the elevation of the chamber comprises retaining the ferromagnetic object at a top of the chamber.

3. The method of claim 1, wherein a platelet activator is present in the chamber.

4. The method of claim 3, wherein no other clot enhancing agent is present in the chamber.

5. The method of claim 1, wherein an anticoagulant is present in the chamber.

6. The method of claim 1, wherein at least a portion of an interior of the chamber is coated with a platelet binding molecule.

7. The method of claim 1, wherein the ferromagnetic object is coated with a platelet binding molecule.

8. The method of claim 1, wherein a plurality of beads comprising a platelet binding molecule are present in the chamber.

9. The method of claim 1, wherein the ferromagnetic object comprises a ferromagnetic washer.

* * * * *